Figure 1:
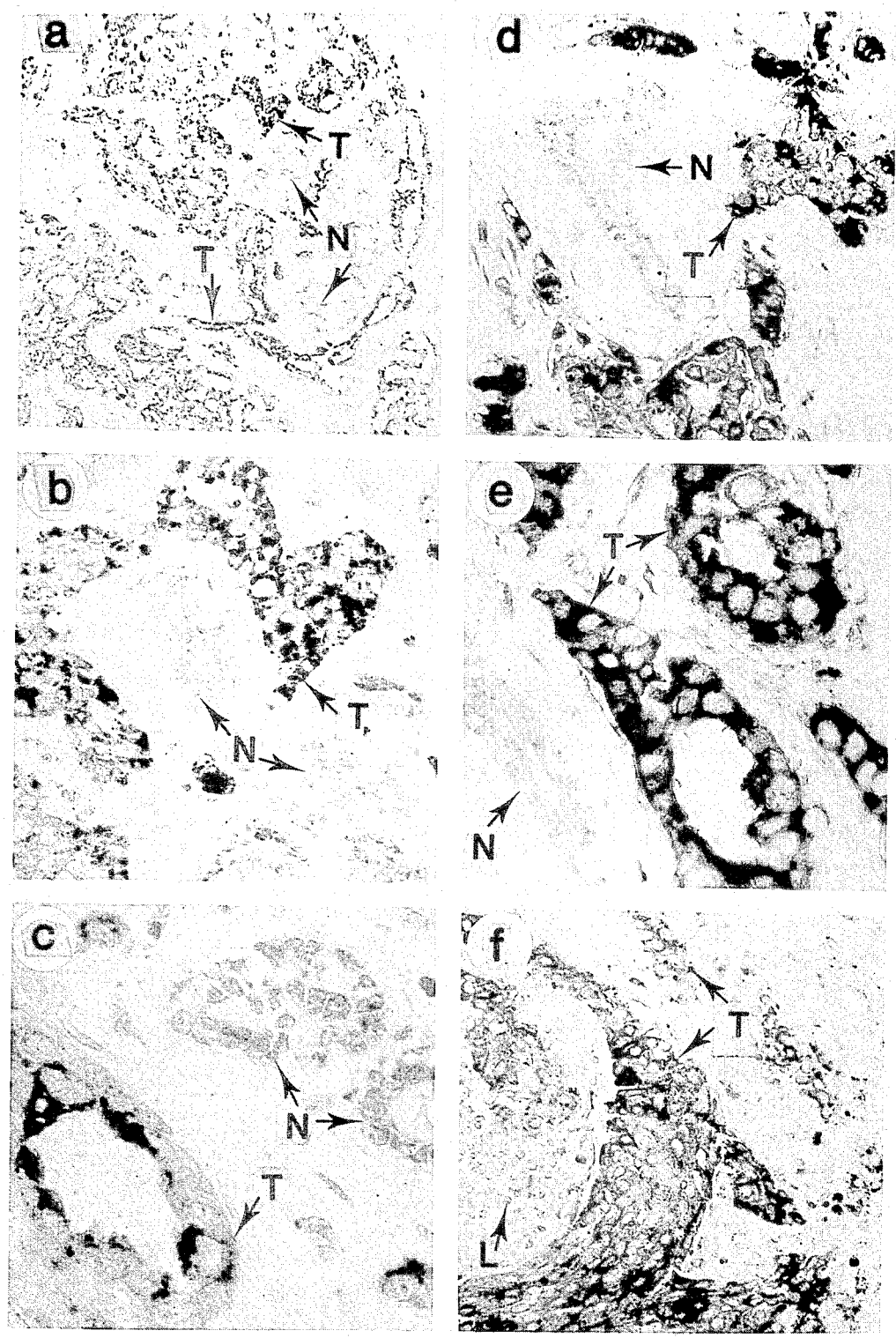

United States Patent [19]

Schlom et al.

[11] Patent Number: 4,522,918

[45] Date of Patent: Jun. 11, 1985

[54] PROCESS FOR PRODUCING MONOCLONAL ANTIBODIES REACTIVE WITH HUMAN BREAST CANCER

[76] Inventors: Jeffery Schlom, 404 Victoria Ct., NW.; David Colcher, 2587 Rambling Rd., both of Vienna, Va. 22180; Marianna Nuti, 9010 Lindale Dr., Bethesda, Md. 20034; Patricia H. Hand, 1113 E. Capital St., SE., Washington, D.C. 20003; Faye Austin, 8204 Toll House Rd., Annandale, Va. 22003

[21] Appl. No.: 330,959

[22] Filed: Dec. 15, 1981

[51] Int. Cl.$^3$ .................... C12P 21/00; C12N 5/00; C12N 15/00; G01N 33/54; A61K 49/00; A61K 39/00; C12R 1/91

[52] U.S. Cl. .................. 435/68; 435/172.2; 435/240; 435/7; 435/948; 436/548; 436/813; 424/85; 424/1.1; 935/93; 935/104; 935/107; 935/110

[58] Field of Search .................. 435/7, 188, 810, 240, 435/241, 172, 68, 948; 424/85, 88, 1.1, 8, 12; 23/230 B; 436/548, 813, 64

[56] References Cited

U.S. PATENT DOCUMENTS

| | | | |
|---|---|---|---|
| 4,172,124 | 10/1979 | Koprowski et al. | 435/172 |
| 4,196,265 | 4/1980 | Koprowski et al. | 435/240 |
| 4,229,426 | 10/1980 | Haagensen, Jr. | 23/230 B |
| 4,232,001 | 11/1980 | Jensen et al. | 23/230 B |
| 4,349,528 | 9/1982 | Koprowski et al. | 424/85 |

OTHER PUBLICATIONS

Stahli et al, "High Frequencies of Antigen Specific Hybridomas: Dependence on Immunization Parameters and Prediction by Spleen Cell...", Journal of Immunological Methods, 32, (1980), pp. 297–304.

Sloane et al, "Distribution of Epithelial Membrane Antigen in Normal and Neoplastic Tissues and its Value in Diagnostic Tumor...", Cancer, 47(4), (1981), pp. 1786–1795.

Schlom et al, "Generation of Human Monoclonal Antibodies Reactive with Human Mammary Carcinoma Cells", Proceedings of the National Academy of Sciences, 77(11), pp. 6841–6845, (1980).

Kohler et al, "Continuous Cultures of Fused Cells Secreting Antibody of Predefined Specificity", Nature, 256, (8–1975), pp. 895–897.

Herzenberg et al, "Cell Hybrids of Myelomas with Antibody Forming Cells and T-Lymphomas with T Cells", Handbook of Experimental Immunology, by Weir, (1979), pp. 25.1–25.7.

Edynak et al, "Fluorescent Antibody Studies of Human Breast Cancer", Journal of the National Cancer Institute, 48, (1972), pp. 1137–1141.

Sternberger et al, "The Unlabled Antibody Enzyme Method Immunocytochemistry of Horomone Receptors at Target Cells," First Int. Symposium on Immunoenzymatic Techniques, (2), (1976), pp. 43–58.

Colcher et al, "A Spectrum of Monoclonal Antibodies Reactive with Human Mammary Tumor Cells", Proceedings of the National Academy of Sciences, 78(5), (5–1981), pp. 3199–3203.

Colcher et al, "Use of Monoclonal Antibodies to Define the Diversity of Mammary Tumor Viral Gene Products in Virons and Tumors," Cancer Research, vol. 41(4), pp. 1253–1277.

Primary Examiner—Thomas G. Wiseman
Assistant Examiner—John Edward Tarcza
Attorney, Agent, or Firm—John S. Roberts, Jr.

[57] ABSTRACT

Monoclonal antibodies demonstrating a reactivity with human breast cancer are produced. The hybridoma cultures secreting immunoglobins are produced by hydridoma technology. Splenic lymphocytes of mice, immunized with membrane-enriched fractions of metastatic human mammary carcinoma tissue are fused with the NS-1 non-immunoglobulin-secreting murine myeloma cell line. Screening of immunoglobulin reactivities and double cloning of cultures yielded 11 monoclonal antibodies that demonstrated activities with the surface of human mammary tumor cells and not with the surface of apparently normal human tissues. These monoclonal antibodies aid in the diagnosis, prognosis and treatment of human breast cancer.

7 Claims, 3 Drawing Figures

PROCESS FOR PRODUCING MONOCLONAL ANTIBODIES REACTIVE WITH HUMAN BREAST CANCER

PRIOR ART STATEMENT

Hybridoma technology was developed by Kohler and Milstein [Kohler, G. and Milstein, C. (1975) *Nature* (London), 256, 494–497].

The technique is also set out in detail in the following excerpt from a basic immunology textbook, Herzenberg and Milstein, *Handbook of Exerimental Immunology*, ed. Weir (Blackwell Scientific, London), 1979, pp. 25.1–25.7.

Assaying for antibody in solid-phase RIA is described by the inventor in Colcher, Horan Hand, Teramoto, Wunderlich, and Schlom, *Cancer Research*, 41, 1451–1459 (1981).

Background art by the inventors is in Colcher, Horan Hand, Nuti, and Schlom, *J. Proc. Natl. Acad. Sci.*, May 1981, Vol. 78, No. 5, 3199–3203.

Patents relating to other tumors produced by hybridoma technology are U.S. Pat. Nos. 4,172,124 and 4,196,265.

UTILITY STATEMENT

These eleven monoclonal antibodies aid in the diagnosis, prognosis, and treatment of human breast cancer. These antibodies are activated only by tumor cells from human mammary cells and not by apparently normal human tissues.

STATEMENT OF DEPOSIT

The following hybridoma cell lines were deposited in the ATCC with the following accession numbers: B6.2, ATCC #HB8106; B25.2, #HB8107; B72.3, #HB8108; F25.2, #HB8109; B38.1, #HB8110; and B50.4, #HB8111.

SUMMARY OF THE INVENTION

Mice were immunized with membrane-enriched fractions of human metastatic mammary carcinoma cells from either of two involved livers (designated Met 1 and Met 2). Spleens of immunized mice were fused with NS-1 myeloma cells to generate 4250 primary hybridoma cultures. Supernatant fluids from these cultures were screened in solid phase RIAs for the presence of immunoglobulin reactive with extracts of metastatic mammary tumor cells from involved livers and not reactive with similar extracts of apparently normal liver. Whereas many cultures demonstrated immunoglobulin reactive with all test antigens, 370 cultures contained immunoglobulin reactive only with the metastatic carcinoma cell extracts. Following passage and double cloning of these cultures by endpoint dilution, the monoclonal immunoglobulins from eleven hybridoma cell lines were chosen for further study. The isotypes of all eleven antibodies were determined; ten were IgG of various subclasses and one was an IgM.

DETAILS OF THE INVENTION

FIG. 1 shows tissue sections and the detection of binding of monoclonal antibodies to human mammary adenocarcinoma cells using the immunoperoxidase technique.

MATERIALS AND METHODS

Cell Extracts

Cell extracts were prepared from breast tumor metastases to the liver from two patients as well as from apparently normal liver. Tissues were minced finely and homogenized for 2 to 3 min. at 4° C. in 10 mM Tris-HCl, (pH 7.2), 0.2 mM $CaCl_2$ (10 gm/100 ml). The homogenate was then subjected to nitrogen cavitation using a cell disruption bomb (Parr Instrument Co., Moline, IL) for 5 min. at 1000 lg/$in^2$ and then clarified at 1000×g for 5 min. Cell membrane enriched fractions were prepared from this extract by centrifugation of the 1000×g supernatant in a discontinuous 20%/40% (w/w, 10 ml of each) sucrose gradient in 10 mM Tris-HCl, (pH 7.2), containing 2 mM CaCL2 for 16 hr at 130,000×g. The material obtained from the 20–40% interface was diluted and pelleted at 130,000×g for 60 min (SW27 rotor, Beckman). The pellet was resuspended in PBS buffer and sonicated at 4° C. for 1 min. at 15 sec. intervals (Branson Sonifier, setting 7). The sonicate was centrifuged at 10,000×g for 10 min. and the supernatant was used for immunizations. The balance of the cell extract was repeatedly passed through columns of Protein A-Sepharose (Pharmacie) to remove cell associated Ig that would interfere with the solid phase radioimmunoassays. Protein concentrations were determined by the Lowry method (Lowry, O. H.; et al, *J. Biol. Chem.*, 193, 265–275, 1951).

Immunizations

Four-week old C57BL/6, BABL/c and C3HfC57BL mice were immunized by intraperitoneal inoculation with 100 μg of membrane-enriched fractions of either of two breast tumor metastases to the liver (termed Met 1 and Met 2) mixed with an equal volume of complete Freund's adjuvant. Fourteen and 28 days later, mice were boosted with an intraperitoneal inoculation of 100 μg of the immunogen mixed with incomplete Freund's adjuvant. After an additional 14 days, 10 μg immunogen was administered intravenously. Spleens were removed for cell fusion 3 to 4 days later.

NS-1 Cells

The preferred embodiment of this procedure requires HL clones. H and L are the heavy and light chains contributed by the antibody producing parental cell. In the past, HL clones were derived from MOPC-21 through the X63-Ag8 myeloma cell line (which secretes an IgG1 myeloma protein). X63-Ag8 also secretes heavy and light chains of G and K. Thus, the hybrid produces a variety of tetrameric molecules with different H, L, G, and K combinations. Only some of these molecules bind to the antigen and even fewer are detectable by a complement dependent reaction.

Fortunately, it has not been difficult to obtain variants of the selected hybrids which have lost the ability to make G and K. By subcloning HLGK lines, HLK clones can be detected and by subcloning these, HL variant clones can be found. The frequency of variants differs from clone to clone but is often in the order of 1–3 percent for each step.

Screening for HL clones can be done in favorable cases simply by haemolytic or cytolytic activity assays, since HL and HLK have greater activity than HLGK. A more general method of screening for HL clones is chain analysis of secreted immunoglobulins (Ig) using acrylamide gels. A convenient method is to intrinsically label the secreted Ig with $^{14}$C-lysine (300 $\mu$c/$\mu$mol/l) in microculture wells are cultured. The cells are centrifuged and the supernatants saved for direct analysis by isoelectric focusing (IEF) or electrophoresis followed by autoradiography after fixing and washing. The focusing positions in IEF analysis for G and K are known and H and L can often be identified as bands with different isoelectric points. This process is complex and time consuming.

To simplify and speed up production of HL clones, rather than using the MOPC-21 variant producing HLGK, a MOPC-21 variant called NS-1 is used. NS-1 does not make G; its initial hybrids are HLK, thus obviating the above procedure as it relates to G.

Hybridoma Methodology

Somatic cell hybrids were prepared using the method of Herzenberg with some modifications. Single cell suspensions of spleen cells from immunized mice were made by passing the tissue through a No. 3 mesh stainless steel screen (B. Fenenco Co., Inc., Norcester, MA). Spleen cells and NS-1 cells were washed in RPMI-1640, containing 2 mM glutamine, 1 mM sodium pyruvate, 50 units/ml penicillin, 50 $\mu$g/ml streptomycin, mixed at a 4:1 ratio, and fused with 50% polyethylene glycol (M.W. 1500) (BDH Chemical Ltd., Poole, England). After fusion, individual wells of 96-well microtiter plates (Costar, Cambridge, MA) were seeded with $1 \times 10^6$ total cells (0.1 ml) of the cell suspension. Fused cells were then selected for growth using RPMI medium as described above containing 15% heat-inactivated fetal calf serum.

Cloning of hybridoma cell lines was performed by limiting dilution. Twenty-four wells of a 96-well microtiter plate (Costar, Cambridge, MA) were seeded with one of the following concentrations of hybridoma cells: 10 cells/well, 5 cells/well, 1 cell/well, or 0.5 cell/well. Mouse thymocytes, derived from the thymus glands of four-week old C57BL/6 mice, were added to each well as feeder cells at a concentration of $10^6$ cells/well. Wells seeded at the concentration that eventually resulted in growth of cells in one out of two wells and containing a single colony of hybridoma cells were chosen for further propagation. All hybridoma cell lines were cloned twice.

Solid Phase Radioimmunoassays

All hybridoma supernatant fluids were assayed for antibody in solid phase RIA usng cell extracts from both breast metastases and normal liver. Fifty microliters of the cell extracts (5 $\mu$g) was added to each well of 96-well microtiter polyvinyl plates and allowed to dry. To minimize non-specific protein absorption, microtiter wells were treated with 100 $\mu$l of 5% bovine serum albumin (BSA) in phosphate buffered saline containing calcium and magnesium (PBS) and incubated for 1 hr. This and all subsequent incubations were at 37° C. The BSA was removed and 50 $\mu$l of hybridoma supernatant fluid was added. After a 1 hr incubation, the unbound Ig was removed by washing the plates with 1% BSA in PBS. The wells were incubated with 50 $\mu$l of a 1:1000 dilution of rabbit anti-mouse IgG F(ab')$_2$ in PBS containing 1% BSA. After 1 hr, the wells were washed three times with 1% BSA in PBS and 50,000 cpm of [$^{125}$I]-labeled Protein A (IPA) in 25 $\mu$l was added to each well. The plates were incubated for an additional hour and the unbound IPA was removed by extensive washing with 1% BSA in PBS. The plates were then subjected to autoradiography using Kodak XR film and Dupont Lighting-Plus intensifying screens. The films were developed after 16 hr at $-70°$ C. The bound IPA was also detected by cutting the individual wells from the plate and measuring the radioactivity in a gamma counter.

Immunoassays for Antibodies to CEA and Ferritin

Solid phase radioimmunoassays for the detection of antibodies to carcinoembryonic antigen (CEA) and ferritin were run as described above with minor modifications. CEA and a mouse monoclonal antibody to CEA was provided by Dr. Hans Hansen (Hoffman-LaRoche, Inc., Nutley, NJ). Thirty nanograms of CEA was applied to each well of the microtiter plate and allowed to dry overnight. The monoclonal antibody to CEA was used as a control with approximately 5000 cpm bound using 1.5 ng of antibody. The assay for ferritin was run using 2 ng of ferritin and rabbit anti-ferritin (both obtained from Calbiochem-Behring, LaJolla, CA). The assay was run as described above, but no second antibody was used on the rabbit anti-ferritin which bound approximately 3500 cpm of IPA at a 1:1000 dilution. A monoclonal antibody to a determinant common to all human HLA, A, B, and C antigens (W6/32) was purchased from Accurate Chemical and Scientific Corp. (Hicksville, NY).

Cells

The BALB/c myeloma cell line, P3-NS1-1-Ag4-1 [NS-1 (see above)], was obtained from Dr. K. J. Kim, NIH, Bethesda, MD. All human cells lines used were obtained from either the American Type Culture Collection, the Breast Cancer Task Force Cell Bank (NCI), the Naval Biosciences Laboratory (Oakland, CA), or the Cell Repository of Meloy Laboratories (Springfield, VA). Cell cultures were maintained as recommended by each laboratory, respectively. Cell lines were tested for species of origin by isoenzyme analyses, karyotyping, and immunofluorescence analyses and were demonstrated to be of proper species identity. These tests were performed by Dr. W. Peterson, Child Research Center of Michigan, via the Biological Carcinogenesis Branch. Cell lines were tested for the presence of *Mycoplasma* species and were negative.

Live Cell Immunoassay

Subconfluent established cell lines were detached from 75 cm$^2$ tissue culture flasks using 0.1% trypsin containing 0.5 mM EDTA (ethylene diamine tetraacetic acid). Cells were then seeded into 96-well, flat bottom tissue culture plates (Limbro Scientific, Inc., Hamden, CT), using the appropriate growth medium at $5 \times 10^4$ cells per well and incubated at 37° C. for 18-24 hrs in a humidified incubator containing 5% CO$_2$. (All additional incubations were performed using identical conditions). The growth medium was then aspirated and 100 $\mu$l of RPMI-1640 containing 10% (w/v) bovine serum albumin (BSA) and 0.08% (w/v) sodium azide were added to each well. After a 30-min. incubation, the fluid was aspirated and the plates were washed with RPMI-1640 with 1% (w/v) BSA and 0.08% (w/v) sodium azide (Wash Buffer). The Wash Buffer was then removed and the plates were inverted to remove excess fluid. All additional washes were performed in this manner. Fifty microliters of Wash Buffer containing 5% (v/v) normal goat serum (Antibodies, Inc., Davis, CA) was then added to each well and the incubation was continued for 30 min. The plates were rinsed with Wash Buffer and 50 µl of monoclonal antibody were added. The plates were incubated for 1 hr and then rinsed twice with Wash Buffer. Fifty microliters of a 1:1000 dilution of rabbit anti-mouse F(ab')$_2$ were then added to each well. The remainder of the assay is as described for the solid phase RIA. At the end of the assay, wells were examined for the presence of cells; more than 95% of the cells were present. Autoradiography was performed as described above. To determine cpm bound, 50 µl of 2 N NaOH were then added to each well. Cotton swabs were then used to absorb the fluid from each well and then were counted in a gamma counter. Background (the average of the cpm obtained with Wash Buffer and NS-1 supernatant fluid) was subtracted from the cpm obtained when monoclonal antibody was used as primary antibody.

Immunoperoxidase Studies

Five micron sections of formalin fixed or frozen sections of tissue on slides were used. Fixed tissues were deparaffinized in xylene and rinsed in absolute ethanol. A 10 min. incubation with 0.3% H$_2$O$_2$ in methanol was used to block any endogenous peroxidase activity. After rinsing in PBS, the slides were incubated with a 1:20 dilution of normal swine serum (NSS) for 15 min. This incubation and all subsequent incubations were carried out at room temperature. The NSS was removed and 0.1 ml monoclonal antibody or normal mouse sera (at an equal or greater immunoglobulin concentration as a control) was placed on the tissue sections and the slides were incubated for 30 min. The antibody was removed and the slides were rinsed for 15 min. in PBS. The slides were then incubated for 30 min. at each step with first a 1:10,000 dilution of goat anti-murine IgG F(ab')$_2$ followed by a 1:200 dilution of swine antigoat and then 1:2000 goat peroxidase antiperoxidase reagent (Cappel Laboratories, Cochranville, PA). The sections were then rinsed in PBS for 15 min. and reacted with 0.06% diaminobenzidine and 0.01% H$_2$O$_2$ for 5 min. The sections were rinsed in PBS, counterstained stained with hematoxylin for 30 sec., dehydrated in ethanol, rinsed in xylene and mounted.

Isotyping of Monoclonal Antibodies

Radial immunodiffusion plates (Meloy Laboratories, Springfield, VA) containing monospecific goat antisera to the murine isotypes were used to determine the isotype and to quantitate the immunoglobulin. Isotypes were also determined using rabbit antisera (Litton Bionetics, Rockville, MD) to specific murine isotypes in solid phase RIAs.

Results:

The primary screen for monoclonal antibodies reactive with human mammary carcinoma cells was a solid phase RIA employing cell extracts of two breast tumor metastases (Met 1 and Met 2) and aparently normal human liver as test antigens. The eleven monoclonal antibodies could immediately be divided into three major groups based on their differential reactivity to Met 1 versus Met 2. Nine of the eleven monoclonals were reactive with both metastases. See Table 1.

TABLE 1

| | | Reactivity of Monoclonal Antibodies in Solid Phase RIAs | | | | | | | | |
|---|---|---|---|---|---|---|---|---|---|---|
| Mcl | | Cell Extracts[a] | | | Live Cells[b] | | | | | |
| | | | | | Mammary Carcinoma | | | | | |
| Ab | Isotype | Met 1[c] | Met 2 | Liver | BT-20 | MCF-7 | ZR-75-1 | Carc.[d] | Sarc.[e] | Normal[f] |
| B6.2 | IgG$_1$ | +++ | ++ | NEG | ++ | +++ | ++ | NEG | NEG | NEG |
| B14.2 | IgG$_1$ | +++ | ++ | NEG | + | ++ | + | NEG | NEG | NEG |
| B39.1 | IgG$_1$ | +++ | ++ | NEG | ++ | ++ | ++ | NEG | NEG | NEG |
| F64.5 | IgG$_{2a}$ | +++ | ++ | NEG | ++ | ++ | + | NEG | NEG | NEG |
| F25.2 | IgG$_1$ | +++ | ++ | NEG | + | + | + | NEG | NEG | NEG |
| B84.1 | IgG$_1$ | +++ | ++ | NEG | + | + | + | NEG | NEG | NEG |
| B38.1 | IgG$_1$ | + | + | NEG | +++ | ++ | +++ | + | NEG | NEG |
| B50.4 | IgG$_1$ | ++ | + | NEG | NEG | + | NEG | NEG | NEG | NEG |
| B50.1 | IgG$_1$ | ++ | + | NEG | NEG | + | NEG | NEG | NEG | NEG |
| B25.2 | IgM | NEG | +++ | NEG | NEG | NEG | NEG | NEG | NEG | NEG |
| B72.3 | IgG$_1$ | +++ | NEG | NEG | NEG | NEG | NEG | NEG | NEG | NEG |
| W6/32 | IgG$_{2a}$ | NEG | NEG | NEG | | + | NEG | +++ | ++ | ++ |
| B139 | IgG$_1$ | +++ | +++ | ++ | ++ | ++ | + | ++ | +++ | ++ |

[a]Solid phase radioimmunoassays were performed as described. NEG, <500 cpm; +, 500–2000 cpm ++, 2001–5000 cpm; +++, >5000 cpm.
[b]The live cell immunoassay was performed on human cells as described. NEG, <300 cpm; +, 300–1000 cpm; ++, 1001–2000 cpm; +++, >2000 cpm.
[c]Mets 1 and 2 are extracts from human metastatic mammary carcinoma cells from involved livers.
[d]The carcinoma cells used were lung (A549), vulva epidermoid (A431) and oral epidermoid (KB).
[e]Rhabdomyosarcoma (A204), fibrosarcoma (HT1080), and melanoma (A375).
[f]Human cells lines were derived from apparently normal breast (Hs0584Bst), skin (Detroit 550), embryonic skin (Detroit 551), fetal lung (WI-38 and MRC-5), fetal testis (Hs0181Tes), fetal hymus (Hs0208Th), fetal bone marrow (Hs0074Bm), embryonic kidney (Flow 4000), fetal spleen (Hs0203Sp), and uterus (Hs0769Ut).

The following groupings are evident.

| Group 1 Monoclonal Antibody | Isotype | Cell extracts | |
|---|---|---|---|
| | | Met 1 | Met 2 |
| B6.2 | IgG1 | +++ | ++ |
| B14.2 | IgG1 | +++ | ++ |
| B39.1 | IgG1 | +++ | ++ |
| F64.5 | IgG2a | +++ | ++ |
| B84.1 | IgG1 | +++ | ++ |
| | IgG1 | + | + |
| | IgG1 | ++ | + |
| | IgG1 | ++ | + |

The above antibodies bind both metastases and all three mammary tumor cell lines (MCF-7, BT-20, ZR75-1). B6.2 binds to a 90,000 d protein.

Group 2

| B25.2 | IgM | Neg | +++ |
|---|---|---|---|

B25.2 binds only Metastase 2.

Group 3

| B72.3 | IgG1 | +++ | Neg |
|---|---|---|---|

B72.3 binds only Metastase 1. B72.3 reacts with a

-continued complex of proteins ranging from 220,000 to 400,000 d.
Group 4
F25.2 has a similar range of reactivity as Group 1 but binds a 220,000 d protein.
Group 5
B38.1 bound to BT-20, MCF-7, ZR-75-1, A 549 lung carcinoma line, A 431 vulva epidermoid carcinoma line and KB oral epidermoid carcinoma line (not to carcinoma and metanoma cell lines tested). Antibody B38.1 thus appears to possess a "pancarcinoma" pattern of binding activity. B38.1 binds to a 70,000 d protein.
Group 6

|        | BT-20 | MCF-7 | 2R-75-1 |
|--------|-------|-------|---------|
| B50.4  | Neg   | +     | Neg     |
| B50.1  | Neg   | +     | Neg     |

B50.4 and B50.1 preferentially bind to the MCF-7 versus the BT-20 cell line. B50.4 binds a 90,000 d protein.

None of the 11 monoclonal antibodies bound to any of the following cell lines derived from apparently normal human tissues; breat, uterus, skin, embryonic skin and kidney, and fetal lung, testis, thymus, bone marrow and spleen. Control monoclonals W6/32 and B129, however, did bind all of these cells.

All eleven antibodies were negative when tested against similar extracts from normal human liver, the A204 rhabdomyosarcoma cell line, the HBL100 cell line derived from cultures of human milk, the Mm5mt/$c_1$ mouse mammary tumor cell line, the C3H10T$\frac{1}{2}$mouse fibroblast cell line, the CrFK feline kidney cell line, and disrupted mouse mammary tumor virus and mouse leukemia virus (Table 1). Two monoclonal antibodies were used as controls in all these studies: (a) W6/32, an anti-human histocompatibility antigen and (b) B139, which was generated against a human breast tumor metastasis, but which showed reactivity to all human cells tested.

The solid phase RIA using cell extracts of metastatic breast tumor cells proved quite sensitive for the detection of test antigen. The assays employed 5 $\mu$g of tissue extract, but titration experiments showed that as little as 0.3 $\mu$g of tissue extract could be used.

Immunoperoxidase Studies

FIG. 1 graphically illustrates the staining.

FIG. 1. Detection of binding of monoclonal antibodies to human mammary adenocarcinoma cells using the immunoperoxidase technique. Tissue sections in panel A through E are from the same area of an infiltrating duct carcinoma. Panel F is an involved axillary lymph node of a patient with an infiltrating duct carcinoma. Panels A, B, and C are tissues stained with monoclonal B50.4. Panels D, E, F are tissues stained with monoclonal B6.2. Panels A-E: Note staining of mammary tumor cells (T), and absence of staining of apparently normal mammary epithelium (N) or stroma. Note the granular staining observed in panels A-C, as compared to the more diffuse staining in panels D and F. Panel F: Note the staining of mammary carcinoma cells (T) and the absence of staining of lymphocytes (L). Panel A is 80×; B is 330×; C is 860×, D is 330×; E is 540×; F is 330×.

To further define specificity and range of reactivity of each of the eleven monoclonal antibodies, the immunoperoxidase technique on tissue sections was employed. As seen in Table 2, all the monoclonals reacted with mammary carcinoma cells of primary mammary carcinomas (both infiltrating ductal and lobular). The percentage of primary mammary tumors that were reactive varied for the different monoclonals, ranging from 74% (23/31) and 80% (8/10) using monoclonals B6.2 and B38.1, respectively, to 22% (2/9) for monoclonal B50.4. In many of the positive primary and metastatic mammary carcnomas, not all tumor cells stained. In certain tumor masses, moreover, heterogeneity of tumor cell staining was observed in different areas of a tumor, and even within a given area (See FIG. 1B). A high degree of selective reactivity with mammary tumor cells, and not with apparently normal mammary epithelium, stroma, blood vessels, or lymphocytes of the breast was observed with all eleven monoclonal antibodies. This is exemplified with monoclonals B50.4 and B6.2 in FIG. 1A-E. A dark reddish-brown stain (the result of the immunoperoxidase reaction with the diaminobenzidine substrate) was observed only on mammary carcinoma cells, whereas only the light blue hematoxylin counterstain was observed on adjacent normal mammary epithelium, stroma, and lymphocytes. Occasionally, a few of the apparently "normal" mammary epithelial cells immediately adjacent to mammary carcinoma cell populations did stain weakly (Table 2). However, apparently normal mammary epithelial cells in distal areas of these same breasts (i.e., where no tumor was present) or from breasts of apparently normal patients were always negative (Table 2). This faint staining of some of the "normal" mammary epithelium immediately adjacent to tumor cells may therefore be the manifestation of antigens shed by adjacent tumor cells, or may represent a "preneoplastic" population expressing the antigen being detected. The staining patterns of mammary carcinoma cells varied among the different monoclonals. This is exemplified in FIG. 1, where it can be seen that monoclonal B50.4 is reactive with mammary carcinoma cells displaying a dense focal staining (FIG. 1A-C). Monoclonal B6.2, on the other hand, reacts with alternate sections of the exact mammary carcinoma displaying a more diffuse pattern. The monoclonal antibodies could also be distinguished from one another on the basis of which mammary tumors they reacted with. For example, monoclonals B72.3 and B6.2 both reacted with infiltrating ductal mammary carcinoma 10970, but only monoclonal B6.2 reacted with mammary tumor 2657, while conversely, only monoclonal B72.3 reacted with mammary tumor 9388. To ensure against artifacts or differences due to sampling of tissues, these experiments were carried out by reacting monoclonals with alternate tissue sections. Frozen sections of primary mammary tumors were also tested with some of the monoclonals; as expected from the surface binding experiments to live cells in culture (Table 1), the frozen sections revealed membrane staining.

Experiments were then carried out to determine if the eleven monoclonals could detect mammary carcinoma cell populations at distal sites; i.e., in metastases. Since the monoclonals were all generated using metastatic mammary carcinoma cells as antigen, it was not unexpected that the monoclonals all reacted, but with different degrees, to various metastases. Perhaps the most efficient of the monoclonals for this purpose was B6.2, which reacted with metastatic mammary carcinoma cells in lymph nodes of 6 of 7 patients but did not react with uninvolved nodes of 8 patients (Table 2). As exemplified in FIG. 1F, none of the monoclonals reacted with normal lymphocytes or stroma from any involved or uninvolved nodes. The eleven monoclonals also varied in their ability to detect metastatic mammary carcinoma lesions in distal sites such as liver, uterus, and bone (Table 2). All eleven monoclonals were negative for reactivity with apparently normal tissues of the following organs: spleens, bone marrow, thyroid, colon, lung, liver, bladder, tonsils, stomach, prostate, and salivary glands (Table 2).

TABLE 2

Reactivity of Monoclonal Antibodies Using the Immunoperoxidase Technique

| Mcl Ab | Mammary Carcinoma | Mammary Epithelium Normal Adjacent | Normal Distal | Normal Nodes | Metastatic Nodes | Distal Metastases | Normal Tissues[a] |
|---|---|---|---|---|---|---|---|
| B6.2  | 23/31 | 6/22[b] | 0/3 | 0/8 | 6/7 | 3/6 | 0/24 |
| B14.2 | 3/4   | 0/2     | NT  | 0/6 | 3/6 | 2/3 | 0/11 |
| B39.1 | 8/11  | 2/5     | 0/2 | 0/4 | 3/4 | 3/6 | 0/16 |
| F64.5 | 2/4   | 0/2     | NT  | 0/5 | 3/5 | 1/5 | 0/12 |
| F25.2 | 3/4   | 1/3     | 0/1 | 0/2 | 1/1 | 1/1 | 0/8  |
| B84.1 | 2/4   | 0/2     | NT  | 0/2 | 0/2 | 1/5 | 0/12 |
| B38.1 | 8/10  | 2/7     | NT  | 0/4 | 1/2 | 2/2 | 0/13 |
| B50.4 | 2/9   | 0/1     | NT  | 0/4 | 2/4 | 1/5 | 0/17 |
| B50.1 | 5/5   | 0/1     | NT  | 0/2 | 0/2 | 2/6 | 0/15 |
| B25.2 | 3/4   | 1/3     | NT  | 0/2 | 1/1 | 1/1 | 0/7  |
| B72.3 | 2/4   | 0/2     | NT  | 0/3 | 1/3 | 0/4 | 0/19 |

[a]Apparently normal thyroid, bone marrow, spleen, colon, lung, liver, bladder, tonsils, kidney, stomach, prostate, salivary gland.
[b]If positive, approximately 2-10% of cells adjacent to tumor stain faintly, whereas distal mammary epithelium of the same breast are negative.

Staining was seen with subpopulations of polymorphonuclear leukocytes with some of the monoclonals. Flourescent activated cell sorter analyses of spleens and bone marrows for various individuals, however, revealed no surface binding of these cells with these same monoclonals.

Immunoperoxidase staining of tissue sections also revealed differences among monoclonals with respect to both the population of cells stained and the staining pattern. None of the monoclonals are reactive with CEA, ferritin, the mouse mammary tumor virus (MMTV) or murine mammary tumor cells infected with MMTV.

Radioimmunodetection Studies

Figure 2A:
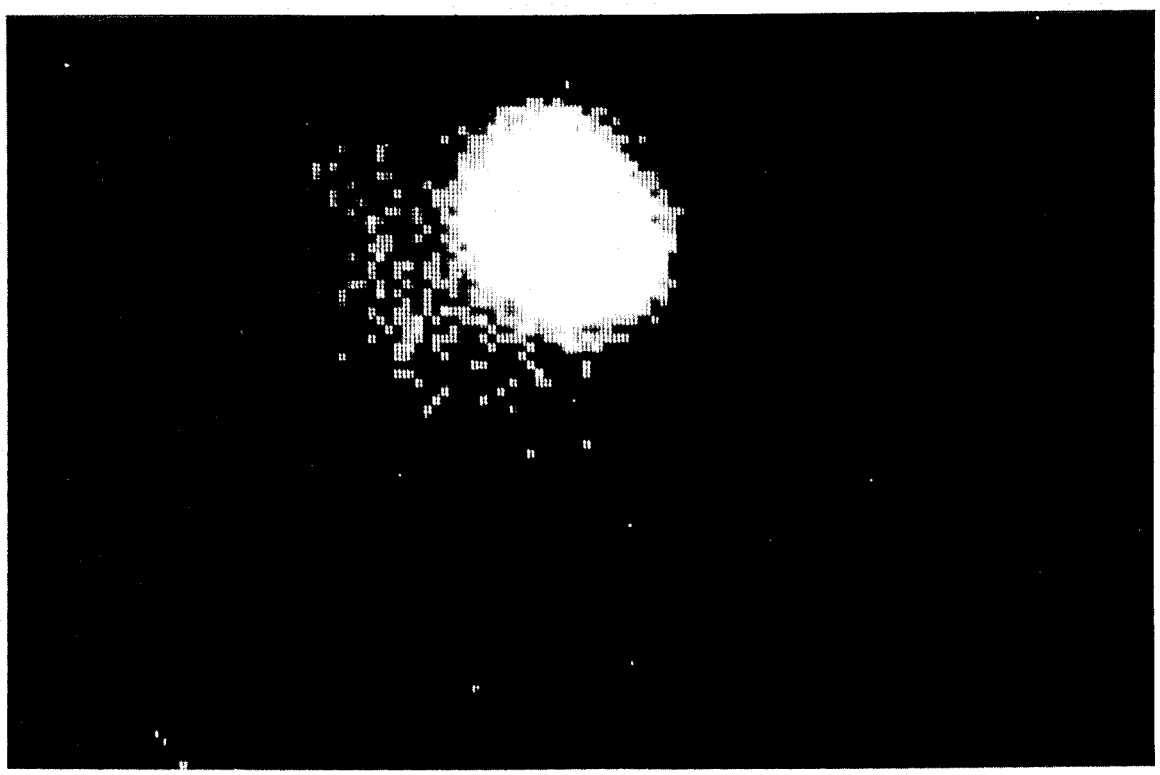
Figure 2B:
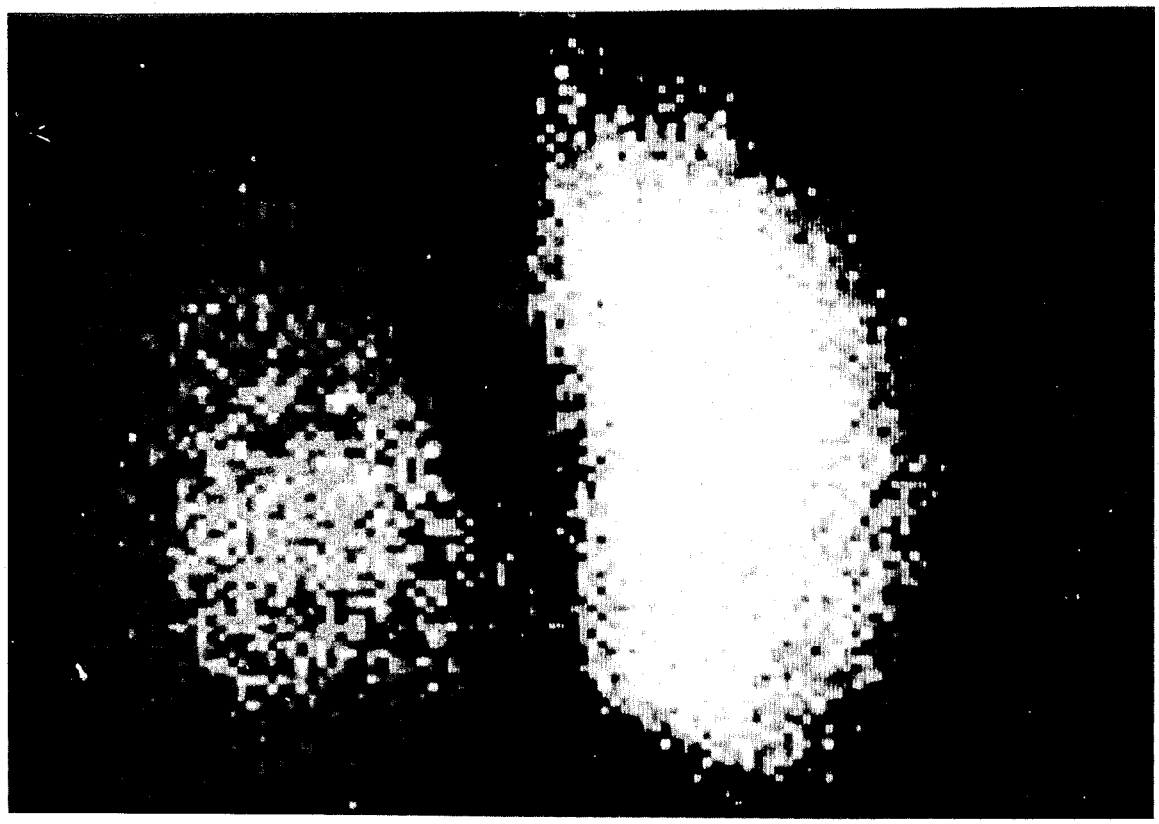

Studies have been undertaken to determine if radiolabeled monoclonal antibodies could be used to detect human mammary tumors growing in athymic mice. Monoclonal B6.2, chosen as the prototype, was labeled with $^{125}I$ using the iodogen technique. Sixty microcuries ($1 \times 10^8$ cpm) of radioactive B6.2 immunoglobulin, Fab' fragments, or F(ab)'$_2$ fragments of B6.2 were then injected intravenously into athymic mice bearing either mammary tumors derived from injections of MCF-7 mammary tumor cells, or the Clouser transplantable human mammary tumor. At 8, 16, 24, 48, 72, and 96 hours post inoculation of radioactive antibody, mice were first scanned with a gamma imager, then sacrificed, and their blood and organs monitored for uptake of radioactive antibody. The ratio of cpm of isotope per gram of tissue for the tumor was from 3:1 to 12:1 versus the blood or normal tissues of tumor bearing animals. When this same radioactive antibody was injected into an athymic mouse bearing a human melanoma, there was no preferential uptake of isotope by the tumor (FIG. 2B). Alternatively, when a radioactive nonspecific immunoglobulin (MOPC-21) was injected into mice bearing transplanted human mammary tumors, there was no preferential uptake of isotope by the tumor. These studies demonstrate the utility of these antibodies in detecting human mammary tumor lesions in an in vivo system.

The eleven monoclonal antibodies (designated B6.2, B14.2, B39.1, F64.5, F25.2, B84.1, B25.2, and B72.3) may be useful in five major areas in the management of human breast cancer. They are:

1. The diagnosis of primary and metastatic breast tumor lesions by the assay of human blood samples or other body fluids for reactivity with any one or a combination of the eleven monoclonal antibodies described.

2. The in-situ detection (via gamma scanning) of primary or metastatic breast tumor lesions by the coupling of one or a combination of the eleven monoclonal antibodies described with radioactive compounds.

3. The treatment of primary or metastatic breast cancer using one or a combination of these eleven antibodies either alone or coupled to toxic drugs, compounds, or radioactive isotopes.

4. The use of one or a combination of the eleven monoclonal antibodies described in the staining (via the immunoperoxidase technique) of populations of tumor cells in thin tissue sections obtained from primary or metastatic breast tumor lesions. This reactivity may serve as a prognostic indicator of the degree of malignancy of those cell populations.

5. The detection of micro-lesions containing only a few tumor cells (in thin tissue sections or body fluids obtained from biopsy of patients suspected of or known to have breast cancer) that would not ordinarily be detected by conventional staining techniques. This would be accomplished with one or a combination of the eleven monoclonal antibodies described using the immunoperoxidase technique described.

Uses

The range of reactivity of the monoclonal antibodies generated and described above allows for the detection of mammary cancer cells, treatments utilizing antibodies, and monitoring of conventional treatments.

The immunoperoxidase technique is useful in the detection of micro-lesions containing only a few tumor cells in thin tissue sections or body fluids obtained from biopsy of patients suspected of, or known to have, breast cancer.

The monoclonal antibodies can be used singly or mixed. The immunoperoxidase technique is as described above.

We claim:

1. A process for producing antibodies from hyridoma cultures comprising the steps of (1) taking splenic lymphocytes of mice previously immunized with membrane-enriched fractions of immunoglobulin-depleted cancer cells;

(2) fusing the lymphocytes with murine myeloma cell line, and (3) culturing the cell line in an in vitro culture medium or in vivo therefor to produce antibodies, which antibody:

(a) reacts and binds with extracts from human metastatic mammary carcinoma cells from involved livers but not with liver cell extracts;

(b) reacts and binds with at least one of the mammary carcinoma cell lines, BT-20, MCF-7, ZR-75-1, but not with lung, vulva epidermoid or oral epidermoid and not with rhabdomyosarcoma, fibrosarcoma and melanoma; and (c) does not react with normal cells derived from breast, skin, lung, bone marrow, kidney, spleen and uterus.

2. The method according to claim 1 wherein said human cancer cells are from metastatic mammary carcinoma in the liver.

3. The method according to claim 1 wherein the depletion is performed using affinity chromatography.

4. The method according to claim 1 wherein the depletion is performed using protein A bound to a solid matrix.

5. The method according to claim 4 wherein said matrix is Sepharose.

6. A process of claim 1 wherein the murine myeloma cell line is non-immunoglobulin secreting murine myeloma cell line designated as NS-1.

7. A method for preparing monoclonal antibody which antibody:

(a) reacts and binds with extracts from human metastatic mammary carcinoma cells from involved livers but not with liver cell extracts;

(b) reacts and binds with at least one of the mammary carcinoma cell lines, BT-20, MCF-7, ZR-75-1, but not with lung, vulva epidermoid or oral epidermoid and not with rhabdomyosarcoma, fibrosarcoma and melanoma; and (c) does not react with normal cells derived from breast, skin, lung, bone marrow, kidney, spleen and uterus, which comprises the steps of:

(1) immunizing mice with membrane enriched fractions of immunoglobulin-depleted cancer cells;

(2) removing the spleens from said mice and making a suspension of spleen cells;

(3) fusing said spleen cells with NS-1 non-immunoglobulin-secreting murine myeloma cell line in the presence of a fusion promoter;

(4) diluting and culturing the fused cells in separate wells in a medium which will not support the unfused cells;

(5) evaluating the supernatant in each well containing a hybridoma for the presence of the desired antibody;

(6) selecting and cloning hybridoma producing the desired antibody; and (7) recovering the antibody from supernatant above said clones.

* * * * *